United States Patent [19]

Inoue et al.

[11] Patent Number: 5,358,876

[45] Date of Patent: Oct. 25, 1994

[54] OXYGEN INDICATOR

[75] Inventors: Yoshiaki Inoue; Hidetoshi Hatakeyama; Isamu Yoshino, all of Tokyo, Japan

[73] Assignee: Mitsubishi Gas Chemical Company, Inc., Tokyo, Japan

[21] Appl. No.: 42,252

[22] Filed: Apr. 2, 1993

Related U.S. Application Data

[63] Continuation-in-part of Ser. No. 914,082, Jul. 16, 1992, abandoned.

[30] Foreign Application Priority Data

Jul. 17, 1991 [JP] Japan .................. 3-202484

[51] Int. Cl.$^5$ .................................. G01N 33/00
[52] U.S. Cl. ................... 436/136; 436/111; 436/138; 436/178; 422/56; 422/57
[58] Field of Search ............... 422/55, 56, 57; 436/136, 138, 178, 111

[56] References Cited

U.S. PATENT DOCUMENTS

| | | | |
|---|---|---|---|
| 4,169,811 | 10/1979 | Yoshikawa et al. | 252/408 |
| 4,357,616 | 11/1982 | Terao et al. | 346/135.1 |
| 4,524,015 | 6/1985 | Takahashi et al. | 252/188.28 |
| 4,526,752 | 7/1985 | Perlman et al. | 422/56 |
| 4,856,650 | 8/1989 | Inoue | 206/204 |
| 5,039,491 | 8/1991 | Saaski et al. | 422/82.05 |
| 5,043,285 | 8/1991 | Surgi | 436/136 |
| 5,047,350 | 9/1991 | Switalski et al. | 436/136 |
| 5,094,959 | 3/1992 | Allen et al. | 436/172 |
| 5,096,813 | 3/1992 | Krumhar et al. | 435/28 |
| 5,124,130 | 4/1992 | Costello et al. | 422/82.06 |

FOREIGN PATENT DOCUMENTS

| | | |
|---|---|---|
| 5-043480 | 3/1980 | Japan . |
| 61-144568 | 7/1986 | Japan . |
| 62-12853 | 1/1987 | Japan . |
| 62-012853 | 1/1987 | Japan . |
| 2-138866 | 3/1988 | Japan . |

OTHER PUBLICATIONS

Abstract of Japanese Patent Application No. 63/187,154, dated Aug. 2, 1988 Derwent Publications Ltd., London, GB.

*Primary Examiner*—Nina Bhat
*Attorney, Agent, or Firm*—Nikaido, Marmelstein, Murray & Oram

[57] ABSTRACT

An oxygen indicator comprising
(a) at least one aliphatic organic compound having 3 or more carbon atoms and containing at least one primary amine group and at least one hydroxy group and optionally an organic or inorganic acid or the chemically bonded material of the organic compound and the acid, and
(b) at least one dyestuff selected from the group consisting of thiazine dyestuffs, indigo dyestuffs and mixtures thereof is disclosed. The oxygen indicator of this invention can be used under anhydrous conditions and under presence of light.

19 Claims, No Drawings

OXYGEN INDICATOR

This application is a continuation-in-part application of U.S. Ser. No. 914,082 filed on Jul. 16, 1992 now abandoned.

BACKGROUND OF THE INVENTION

1. Field of the Invention

The present invention relates to an oxygen indicator indicating the presence or absence of oxygen in a gaseous atmosphere for maintaining foodstuffs, electronic parts, electrical products having electronic parts, metallic parts or products having metallic parts.

By the "oxygen indicator" in the specification and claims is meant an oxygen indicator composition, a tablet comprising an oxygen indicator composition and film or sheet on which an oxygen indicator composition is coated. The presence or substantial absence of oxygen in the gaseous atmosphere surrounding the indicator is indicated by reversible color change of the indicator.

2. Prior Art

U.S. Pat. Nos. 4,169,811 and 4,349,509 disclose an oxygen indicator containing a reducing agent glucose. However, water or moisture is necessary for these indicators to exhibit the function of the Indicator. When these indicators are used under anhydrous conditions, the function of the indicator is not sufficiently exhibited.

Even when water is previously added to the oxygen indicator in order to avoid the Inconvenience, the moisture is absorbed in a desiccant or a dried foodstuff, whereby the function of the indicator is reduced. In addition, the water in the indicator moistens the dried foodstuffs to be maintained in good state.

Japanese Patent Publication (Kokai) Nos. 61-144568 and 62-12853 disclose an oxygen indicator comprising a thiazine dyestuff and an organic acid salt of ethanol amine as essential components in order to overcome the above mentioned shortcoming. However, when the oxygen indicator is exposed to light, there is possibility that the indicator will show the color indicating the absence of oxygen in spite of the presence of small amount of oxygen.

In other words, prior oxygen indicators do not sufficiently function in the absence of moisture or when exposed to light.

SUMMARY OF THE INVENTION

The oxygen indicator of the present invention overcomes the above mentioned shortcoming.

An object of the present invention is to provide an oxygen indicator which functions under anhydrous conditions or when exposed to light.

This invention relates to an oxygen indicator comprising:
(a) at least one aliphatic organic compound having 3 or more carbon atoms and containing at least one primary amine group and at least one hydroxy group, and
(b) at least one dyestuff selected from the group consisting of thiazine dyestuffs, indigo dyestuffs and mixtures thereof.

The indicator may further contain an organic acid or an inorganic acid. The organic compound and the organic acid or the inorganic acid may be chemically bonded to each other.

DETAILED DESCRIPTION OF THE INVENTION

The aliphatic organic compound (sometimes hereinafter referred to as main component) having 3 or more carbon atoms and containing at least one primary amine group and at least one hydroxy group changes the color of the dyestuff in the absence of oxygen. The primary amine group and the hydroxy group in the organic compound are functional groups for changing the color of the dyestuff in the absence of oxygen. The function of these groups is not affected by the other group which may be present in the organic compound. All of the aliphatic organic compound having 3 or more carbon atoms and containing a primary amine group and a hydroxy group can be used in the present invention. Usually, organic compounds having a lower molecular weight are preferred for use. Oligomeric or polymeric compounds may also be used.

Since compounds having 1 or 2 carbon atoms are very volatile, these compounds are likely to be volatilized during the storage of the indicator containing the compound, whereby the function of the indicator is lowered. The compounds are also odorous. It has been proposed to use a compound having 1 or 2 carbon atoms with an organic acid or an inorganic acid in order to lower its volatility. However, the function of the oxygen indicator containing the organic compound having 1 or 2 carbon atoms and an organic acid or an inorganic acid is instable. The indicator is practically inconvenient.

Examples of the aliphatic organic compounds having 3 or more carbon atoms and containing at least one primary amine group and at least one hydroxy group include 3-amino-1,2-propanediol, 3-amino-1-propanol, 3-amino-2-propanol, 4-amino-3-butanol, 4-amino-1-butanol, 5-amino-4-pentanol, 5-amino-1-pentanol, 6-amino-5-hexanol, 6-amino-1-hexanol, glucosamine and 3-amino-1,2-butanediol.

Aliphatic organic compounds having 3 or more carbon atoms in which a carbon atom having the primary amine group adjacent to a carbon atom having a hydroxy group are more preferred. Of these aliphatic organic compounds, 3-amino-1,2-propanediol, 3-amino-2-propanol, 4-amino-3-butanol, 5-amino-4-pentanol, 6-amino-5-hexanol, glucosamine and 3-amino-1,2-butanediol are preferred.

The aliphatic organic compound may be used together with at least one organic acid or an inorganic acid in which case odor and volatility are minimized. The aliphatic organic compound and the organic acid or the inorganic acid may form a salt or an adduct.

Examples of the inorganic acids that may be used in the present invention include sulfuric acid, nitric acid, phosphoric acid, silicic acid and the like. Examples of the organic acids include aliphatic acids and sulfonic acids.

The dyestuffs make the reversible color change that occurs between conditions where oxygen is present and conditions where oxygen is absent in the presence of an electron donor. That is, the dyestuffs become colorless or change to another color in the substantial absence of oxygen. The dyestuffs include thiazine dyestuffs and indigo dyestuffs.

Thiazine dyestuffs are represented by the formula

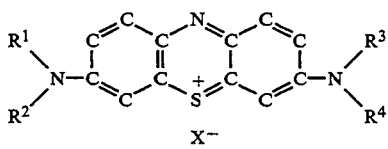

wherein $R^1$-$R^4$ are independently alkyl or hydrogen and X is halogen.

Indigo dyestuffs are represented by the formula

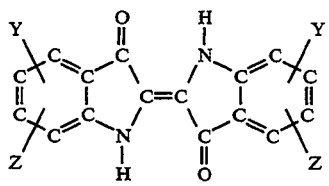

wherein Y is independently H, Br or $SO_3Na$ and Z is independently H, Br or $SO_3Na$.

Examples of the thiazine dyestuffs include Lauth's Violet, Azure B, Azure C, Methylene Blue, and Thionine Blue having thiazine ring as well as Neomethylene Blue and Brilliant Alizarine Blue in which an —OH group and/or $S_3H$ is present on tile nuclear carbon atoms.

Examples of the indigo dyestuffs include Indigo, Indigo Carmine, Bromo Indigo R and the like.

A dyestuff which does not exhibit a color change according to presence or absence of oxygen may be used together with the thiazine or indigo dyestuff in order to give rise to a clearer color change.

The form of the oxygen indicator used in the present invention is not particularly limited. Since the oxygen indicator is placed with an oxygen scavenger and an object product to be stored in a hermetic system, it is preferred that the oxygen indicator be in the form of a tablet or be printed on paper, non-woven fabric sheet or film.

An inorganic filler, such as silicate or a polymer may be added to the oxygen indicator in the form of a tablet in order to ensure the strength of the tablet. Stearic acid salts (lubricant) and the main component are supported by the filler. The tablet comprising the main component and the other components may be prepared by conventional molding methods.

When the oxygen indicator is printed on a substrate, a binder, such as ethyl cellulose, polyvinyl alcohol or starch and a pigment, such as calcium carbonate, titanium oxide or barium sulfate may be added to the printing composition in order to ensure the adhesion between the main component/the dyestuff and tile substrate. As occasion, a polyhydric alcohol, such as glycerine or polyethylene glycol may be added to the main component and the dyestuff be added to water or an organic solvent, after which the resulting liquid material may be coated on a film or sheet and dried to obtain the oxygen indicator.

The oxygen indicator composition may be printed on a substrate. Alternatively the oxygen indicator composition may be printed on a package for an oxygen scavenger, or a packaging material or a package container for material to be stored.

When the oxygen indicator composition is printed on a package bag or container, it is preferably printed on the inside of an transparent film having an oxygen barrier property, followed by laminating a film having an oxygen permeability of not less than 1000 ml/$m^2$·Atm·day on the indicator layer.

The oxygen indicator of the present invention may be packed in a bag formed of an oxygen permeable film of not less than 1000 ml/$m^2$·Atm·day. Examples of the oxygen permeable films include perforated or non-perforated polyethylene, silicone resin, polypropylene, vinyl acetate-ethylene copolymer or polypropylene. The package containing the oxygen indicator may be packed in another bag with the object material to be stored. In this case, direct contact between the oxygen indicator and the object material to be stored can be avoided, so the object material is not contaminated. When the oxygen indicator is packed in an oxygen permeable bag, the oxygen diffusion rate can be adjusted, whereby the color change rate of the oxygen indicator can be adjusted.

Films having an oxygen barrier property include a polyvinylidene chloride-coated film and films deposited with silicon oxide.

The present invention is further illustrated by the following non-limiting examples. The percentages and parts are by weight, unless otherwise specified.

EXAMPLES 1-32

Preparation of Oxygen Indicator Composition

The components given in Table 1 were added to ethyl alcohol or toluene, followed by agitating the mixture by high speed homomixer to allow the components to be dissolved or be dispersed in the solvent, thereby obtaining the oxygen indicator compositions in which the components are uniformly dispersed in the solvent.

TABLE 1

| Ex. No. | main component | acid | dyestuff 1 | dyestuff 2 | binder | pigment | polyhydric alcohol | solvent |
|---|---|---|---|---|---|---|---|---|
| 1 | APD | OL | MB | | EC | TiO$_2$ | GC | ethanol |
| | 25 g | 78 g | 2 g | | 80 g | 150 g | 10 g | 520 g |
| 2 | ABD | OL | MB | | EC | TiO$_2$ | | ethanol |
| | 24 g | 78 g | 2 g | | 80 g | 150 g | | 520 g |
| 3 | AB1N | OL | MB | | EC | TiO$_2$ | | ethanol |
| | 27 g | 78 g | 2 g | | 80 g | 150 g | | 520 g |
| 4 | APE1N | OL | MB | | EC | TiO$_2$ | GC | ethanol |
| | 30 g | 78 g | 2 g | | 80 g | 150 g | 10 g | 520 g |
| 5 | AH1N | OL | MB | | EC | TiO$_2$ | GC | ethanol |
| | 34 g | 78 g | 2 g | | 80 g | 150 g | 10 g | 520 g |
| 6 | GCA | OL | MB | | EC | TiO$_2$ | | ethanol |
| | 25 g | 78 g | 2 g | | 80 g | 150 g | | 520 g |
| 7 | APD | OL | TI | | EC | TiO$_2$ | | ethanol |
| | 38 g | 78 g | 2 g | | 80 g | 150 g | | 520 g |
| 8 | APD | OL | AC | | EC | TiO$_2$ | | ethanol |

TABLE 1-continued

| Ex. No. | main component | acid | dyestuff 1 | dyestuff 2 | binder | pigment | polyhydric alcohol | solvent |
|---|---|---|---|---|---|---|---|---|
|  | 38 g | 78 g | 2 g |  | 80 g | 150 g |  | 520 g |
| 9 | APD | OL | NMB |  | EC | TiO$_2$ |  | ethanol |
|  | 38 g | 78 g | 2 g |  | 80 g | 150 g |  | 520 g |
| 10 | APD | OL | BAAM | RVO | EC | TiO$_2$ |  | ethanol |
|  | 38 g | 78 g | 2 g | 1.4 g | 80 g | 150 g |  | 520 g |
| 11 | APD | OL | MB | ACD | EC | TiO$_2$ |  | ethanol |
|  | 38 g | 78 g | 2 g | 1.4 g | 80 g | 150 g |  | 520 g |
| 12 | APD | LA | MB |  | EC | TiO$_2$ |  | ethanol |
|  | 38 g | 84 g | 2 g |  | 80 g | 150 g |  | 520 g |
| 13 | AP1N | HCL | MB |  | EC | TiO$_2$ |  | ethanol |
|  | 25 g | 14 g | 2 g |  | 80 g | 150 g |  | 520 g |
| 14 | AB1N | OL | MB |  | EC | — |  | ethanol |
|  | 25 g | 78 g | 2 g |  | 80 g |  |  | 520 g |
| 15 | APEN | OL | MB |  | EC | CaCO$_3$ |  | ethanol |
|  | 24 g | 78 g | 2 g |  | 80 g | 150 g |  | 520 g |
| 16 | ABN | OL | MB |  | PVA | CaCO$_3$ | GC | ethanol |
|  | 25 g | 78 g | 2 g |  | 80 g | 150 g | 10 g | 520 g |
| 17 | APEN | OL | MB |  | starch | CaCO$_3$ | GC | ethanol |
|  | 24 g | 78 g | 2 g |  | 80 g | 150 g | 10 g | 520 g |
| 18 | APD | OL | IC |  | starch | CaCO$_3$ |  | ethanol |
|  | 25 g | 78 g | 2 g |  | 80 g | 250 g |  | 520 g |
| 19 | APD | STA | MB |  | EC | TiO$_2$ |  | ethanol |
|  | 38 g | 84 g | 2 g |  | 80 g | 150 g |  | 520 g |
| 20 | APD | OL | MB |  | PVA | TiO$_2$ |  | ethanol |
|  | 38 g | 84 g | 2 g |  | 80 g | 150 g |  | 520 g |
| 21 | APD | OL | MB |  | CR | TiO$_2$ |  | toluene |
|  | 38 g | 84 g | 2 g |  | 80 g | 150 g |  | 520 g |
| 22 | AP1N | OL | MB |  |  |  | GC | ethanol |
|  | 38 g | 84 g | 2 g |  |  |  | 10 g | 520 g |
| 23 | AP2N | OL | MB |  |  |  | GC | ethanol |
|  | 38 g | 84 g | 2 g |  |  |  | 10 g | 520 g |
| 24 | APD | OL | MB | ACD | EC | TiO$_2$ | GC | ethanol |
|  | 25 g | 78 g | 2 g | 2 g | 80 g | 150 g | 10 g | 520 g |
| 25 | AP2N | OL | MB | ACD | EC | TiO$_2$ | GC | ethanol |
|  | 25 g | 70 g | 2 g | 2 g | 80 g | 150 g | 10 g | 520 g |
| 26 | AB3N | OL | MB | ACD | EC | TiO$_2$ | GC | ethanol |
|  | 25 g | 65 g | 2 g | 2 g | 80 g | 150 g | 10 g | 520 g |
| 27 | AH5N | OL | MB | ACD | EC | TiO$_2$ | GC | ethanol |
|  | 25 g | 62 g | 2 g | 2 g | 80 g | 150 g | 10 g | 520 g |
| 28 | APE4N | OL | MB | ACD | EC | TiO$_2$ | GC | ethanol |
|  | 25 g | 58 g | 2 g | 2 g | 80 g | 150 g | 10 g | 520 g |
| 29 | AP1N | OL | MB | ACD | EC | TiO$_2$ | GC | ethanol |
|  | 25 g | 78 g | 2 g | 2 g | 80 g | 150 g | 10 g | 520 g |
| 30 | AB1N | OL | MB | ACD | EC | TiO$_2$ | GC | ethanol |
|  | 31 g | 78 g | 2 g | 2 g | 80 g | 150 g | 10 g | 520 g |

Main Component
APD: 3-amino-1,2-propanediol
AP1N: 3-amino-1-propanol
AP2N: 3-amino-2-propanol
AB1N: 4-amino-1-butanol
AB3N: 4-amino-3-butanol
APE1N: 5-amino-1-pentanol
APE4N: 5-amino-4-pentanol
AH1N: 6-amino-1-hexanol
AH5N: 6-amino-5-hexanol
GCA: glucosamine
ABD: 4-amino-1,2-butanediol
Acid
OL: oleic acid
LA: lauric acid
HCL: hydrochloric acid
STA: stearic acid
Dyestuff
MB: Methylene Blue
TI: Thionine
AC: Azure C
NMB: Neomethylene Blue
BAAB: Brilliant Arizarine Blue
RVO: Lauth's Violet
ACD: Acidred
IC: Indigocarmine
Binder
EC: ethyl cellulose
PVA: polyvinyl alcohol
PAV: polyvinyl acetate
CR: chlororubber
Polyhydric alcohol
GC: glycerine
TME: trimethylol ethane
PEG: polyethylene glycol

EXAMPLES 31–62

Printing Oxygen Indicator Composition to Substrate

The indicator compositions prepared in Examples 1–30 were coated on the substrates shown in Table 2 by means of a Meyer bar, and dried at 100° C. for 45 seconds under hot air.

TABLE 2

| Ex. | Examples of indicator | substrate | coating amount g/m² |
|---|---|---|---|
| 31 | 1 | neutral paper | 5 |
| 32 | 1 | film | 3 |
| 33 | 1 | non-woven fabric | 3 |
| 34 | 2 | neutral paper | 6 |
| 35 | 3 | neutral paper | 5 |
| 36 | 4 | neutral paper | 3 |
| 37 | 5 | neutral paper | 6 |
| 38 | 6 | neutral paper | 6 |
| 39 | 7 | neutral paper | 6 |
| 40 | 8 | neutral paper | 6 |
| 41 | 9 | neutral paper | 5 |
| 42 | 10 | neutral paper | 3 |
| 43 | 11 | neutral paper | 6 |
| 44 | 12 | neutral paper | 6 |
| 45 | 13 | neutral paper | 5 |
| 46 | 14 | neutral paper | 3 |
| 47 | 15 | neutral paper | 6 |
| 48 | 16 | neutral paper | 3 |
| 49 | 17 | neutral paper | 6 |
| 50 | 18 | neutral paper | 3 |
| 51 | 19 | neutral paper | 5 |
| 52 | 20 | neutral paper | 5 |
| 53 | 21 | neutral paper | 5 |
| 54 | 22 | neutral paper | 5 |
| 55 | 23 | neutral paper | 5 |
| 56 | 24 | neutral paper | 5 |
| 57 | 25 | neutral paper | 5 |
| 58 | 26 | neutral paper | 5 |
| 59 | 27 | neutral paper | 5 |
| 60 | 28 | neutral paper | 5 |
| 61 | 29 | neutral paper | 5 |
| 62 | 30 | neutral paper | 5 |

EXAMPLES 64–87

Function of Oxygen Indicator

Each of the oxygen indicators prepared in Examples 31–55 was sealed with an oxygen scavenger and air (250 ml) in KON/PE bag (150 mm×200 mm). The bags were maintained at 25° C. at a distance of 1 meter from 40 W fluorescent tube. The oxygen concentration and humidity in the system and change of color of oxygen indicator with time are shown in Table 3.

The oxygen scavenger was prepared by a process which comprises impregnating a mixture of iron 11linoleate (0.5 g) and soybean oil (3 g) into particulate activated carbon (10 g), and packing the resulting particles and silicagel A type (15 g) by a bag (60×90 mm) formed of paper/perforated polyethylene.

Control Run 1

Glucose (5 g), Methylene Blue (MB) (0.2 g) and Acid Red (ACD) (0.2 g) were added to a 50% aqueous solution of ethanol (45 g) in the order of description. The mixture was agitated by high speed agitator to obtain a uniform solution. Mg(OH)$_2$ (35 g) and magnesium stearate (8 g) were added to the solution in the order of description. The resulting mixture was uniformly agitated. The mixture was dried at 80° C. for 35 minutes to obtain particles. The resulting particles were placed in a cavity having a diameter of 7 mm and a depth of 10 mm and pressed under a load of 300 Kg to obtain a tablet having a thickness of 4 mm. The function of the resulting tablet as an oxygen indicator was tested as in Examples 63–87. The results are shown in Table 3.

Control Run 2

The procedure of Example 31 was repeated except that triethanol amine was used instead of 3-amino-1,2-propanediol employed in Example 1, thereby preparing an oxygen indicator. The resulting oxygen indicator was tested as in Examples 63–87. The results are shown in Table 3.

TABLE 3

| Ex. No. | oxygen indicator | 0 hr. | 12 hrs. | 24 hrs. | 14 days | 1 month |
|---|---|---|---|---|---|---|
| O$_2$ conc. in the system | | 20.9 | 3.5 | 0.0 | 0.0 | 0.0 |
| relative humidity in the system % | | 70 | 4 | 2 | 1 | 1 |
| 63 | 31 | B | B | R | R | R |
| 64 | 32 | B | B | BR | R | R |
| 65 | 33 | B | B | BRR | R | R |
| 66 | 34 | B | B | BR | R | R |
| 67 | 35 | B | B | BR | R | R |
| 68 | 36 | B | B | BR | R | R |
| 69 | 37 | B | B | BRR | R | R |
| 70 | 38 | B | B | R | R | R |
| 71 | 39 | B | B | BR | R | R |
| 72 | 40 | B | B | R | R | R |
| 73 | 41 | B | B | BRR | R | R |
| 74 | 42 | B | B | R | R | R |
| 75 | 43 | B | B | R | R | R |
| 76 | 44 | B | B | BR | R | R |
| 77 | 45 | B | B | BRR | R | R |
| 78 | 46 | B | B | BRR | R | R |
| 79 | 47 | B | B | BR | R | R |
| 80 | 48 | B | B | BR | R | R |
| 81 | 49 | B | B | BR | R | R |
| 82 | 50 | B | B | BRR | R | R |
| 83 | 51 | B | B | R | R | R |
| 84 | 52 | B | B | BRR | R | R |
| 85 | 53 | B | B | R | R | R |
| 86 | 54 | B | B | BR | R | R |
| 87 | 55 | B | B | R | R | R |
| Control Run 1 | | B | B | BR | R | BBR |
| Control Run 2 | | B | R | R | R | R |

Color changes in O$_2$ indicator

| B | BBR | BR | BRR | R |
|---|---|---|---|---|
| blue | | blue violet or light blue | | red or white |

20% ← ← —O$_2$ conc. %— ← ←0%

When the oxygen indicator of the present invention was maintained for 24 hours or more under anhydrous state, while being irradiated with a light and in the absence of oxygen, the color of the indicator showed BR, BRR or R meaning the absence of oxygen. Even when the indicator was maintained under the above conditions for one month, the color of the indicator showed "R".

On the other hand, the indicator of Control Run 1 once changed to BR or R expressing the absence of oxygen. However, when the indicator was maintained under dried state for one month, the indicator returned BBR expressing the presence of oxygen in spite of the absence of oxygen.

The indicator of Control Run 2 showed R expressing the absence of oxygen under the presence of light in spite of the presence of oxygen in a concentration of 3.5%.

EXAMPLES 88-94

Function of Oxygen Indicator

The oxygen indicators prepared in Examples 56-62 were cut to a size 20 mm×20 mm. Each of the oxygen indicators were sealed in the bag (150 mm×200 mm) formed of silicon oxide-deposited firm with an oxygen scavenger and air (250 ml). The bag was adhered to a window glass which was irradiated to sun light and was maintained at 25° C. The oxygen concentration and humidity in the system and the color change of the indicator with time are shown in Table 5.

The oxygen scavenger was prepared by a process which comprises impregnating a mixture of iron linoleate (0.5 and soybean oil (3 g) into particulate activated carbon (10 g), and packing the resulting particles and quick lime (15 g) by a bag (60×90 mm) formed of paper/perforated polyethylene.

Control Run 3

Glucose (5 g), Methylene Blue (MB) (0.2 g) and Acid Red (ACD) (0.2 g) were added to a 50% aqueous solution of ethanol (45 g) in the order of description. The mixture was agitated by high speed agitator to obtain a uniform solution. $Mg(OH)_2$ (35 g) and magnesium stearate (8 g) were added to the solution in the order of description. The resulting mixture was uniformly agitated. The mixture was dried at 80° C. for 35 minutes to obtain particles. The resulting particles were placed in a cavity having a diameter of 7 mm and a depth of 10 mm and pressed under a load of 300 Kg to obtain tablets having a thickness of 4 mm. The function of the resulting tablet as an oxygen indicator was tested as in Examples 88-94. The results are shown in Table 4.

Control Run 4

The procedure of Example 31 was repeated except that triethanol amine was used instead of 3-amino-1,2-propanediol employed in Example 1, thereby preparing an oxygen indicator. The resulting oxygen indicator was tested as in Examples 88-94. The results are shown in Table 4.

TABLE 4

| Ex. | oxygen indicator employed | 0 hr. | 12 hrs. | 18 hrs. | 24 hrs. | 14 days | 1 month |
|---|---|---|---|---|---|---|---|
| | $O_2$ conc. in the system % | 20.9 | 3.1 | 0.2 | 0.0 | 0.0 | 0.0 |
| | humidity in the system RH % | 71 | 2 | 1 or less | 1 or less | 1 or less | 1 or less |
| 88 | Ex. 56 | B | B | BR | R | R | R |
| 89 | Ex. 57 | B | B | BBR | R | R | R |
| 90 | Ex. 58 | B | B | BBR | R | R | R |
| 91 | Ex. 59 | B | B | BR | R | R | R |
| 92 | Ex. 60 | B | B | BBR | R | R | R |
| 93 | Ex. 61 | B | B | B | BR | R | R |
| 94 | Ex. 62 | B | B | B | BR | R | R |
| | Control Run 3 | B | B | BBR | R | R | BBR |
| | Control Run 4 | B | R | R | R | R | R |

TABLE 4-continued

| | 0 hr. | 12 hrs. | 18 hrs. | 24 hrs. | 14 days | 1 month |
|---|---|---|---|---|---|---|
| Run 4 | | | | | | |

Note: Color changes in $O_2$ indicator
B — BBR — BR — BRR — R
blue — — blue violet or light blue — — red or white 20% ← ← — $O_2$ conc. % — → ← ← 0%

EXAMPLE 95

The oxygen indicator composition of Example 1 was printed in a 5 mm circle in a coating amount of 3 g/m² on the non-coated surface of a polyvinylidene (2 μm thick) coated oriented nylon film 15 μm thick by means of gravure printing and dried at 100° C. for 45 seconds. A 5% isocyanate adhesive dissolved in ethyl acetate was coated in a coating amount of 3 g/m² on the printing surface of the oxygen indicator composition-printed film and thermal-treated at 95° C. for 24 hours; and then polyethylene film 55 micron meter thick was laminated on the adhesive layer.

The bag (150×200 mm) was prepared from the resulting film. The function of the indicator was tested as in Example 63. The results are shown in Table 5.

TABLE 5

| Ex. 95 | 0 hr. | 12 hrs. | 24 hrs. | 14 days | 1 month |
|---|---|---|---|---|---|
| $O_2$ conc. in the system % | 20.9 | 3.5 | 0.0 | 0.0 | 0.0 |
| relative humidity in the system % | 70 | 4 | 2 | 1 | 1 |
| color of indicator | B | B | BRR | R | R |

The $O_2$ indicator experienced color changes at a slightly slower speed than the indicator of Example 63 but not so slowly as to cause a problem in practice.

EXAMPLE 96

3-Amino-1,2-propanediol (APD) (2 g), oleic acid (OL) (8 g), Methylene Blue (MB) (0.2 g) and glycerine (GC) (8 g) were added to ethanol (52 g) in tile order of description. The mixture was agitated by high speed agitator to obtain a uniform solution. Silicon oxide (white filler) (500 g) and magnesium stearate (8 g) were mixed with the mixture. The resulting oxygen indicator particles were placed into a cavity having a diameter of 7 mm and a depth of 10 mm and pressed under a load of 300 Kg to obtain tablets having a thickness of 4 mm. The Function of the resulting oxygen indicator tablet was tested as in Example 63. The function of the tablet was the same as that of the indicator prepared in Example 63.

EXAMPLES 97-99

The oxygen indicator prepared in Example 43 was cut to a size 20 mm×20 mm. The oxygen indicator was adhered on the inside of the bag (250 mm×300 mm) Formed of polyvinylidene chloride-coated oriented nylon composite film; and an oxygen scavenger, desiccant and air 250 ml were placed in the bag; and the bag was sealed. The resulting bag was maintained at 25° C. at places which are irradiated at different intensity of light. The oxygen concentration and humidity in the system and the color change of the indicator are shown in Table 6.

The oxygen scavenger was the same as that used in Example 63. The desiccant was the one obtained by packing silicagel (A type) (20 g) with a perforated polyethylene package (75 mm×100 mm).

Control Runs 5–7

The procedures of Examples 97–99 were repeated except that the oxygen indicator of Control Run 1 was used. The results are shown in Table 6.

Control Runs 8–10

The procedures of Examples 97–99 were repeated except that tile oxygen indicator of Control Run 2 was used. The results are shown in Table 6.

TABLE 6

| Ex. | oxygen indicator employed | illumination intensity lux | Storage time | | | | |
|---|---|---|---|---|---|---|---|
| | | | 0 hr. | 12 hrs. | 24 hrs. | 14 days | 1 month |
| | O$_2$ conc. in the system % | | 20.8 | 1.5 | 0.0 | 0.0 | 0.0 |
| | humidity in the system RH % | | 75 | 1 | 1 or less | 1 or less | 1 or less |
| 97 | Ex. 47 | 50 | B | B | BR | R | R |
| 98 | Ex. 47 | 750 | B | B | BRR | R | R |
| 99 | Ex. 47 | 3500 | B | B | BRR | R | R |
| Cont. Run 5 | Control Run 1 | 50 | B | B | BRR | R | BBR |
| Cont. Run 6 | Control Run 1 | 750 | B | B | BRR | R | BBR |
| Cont. Run 7 | Control Run 1 | 3500 | B | B | BRR | R | BBR |
| Cont. Run 8 | Control Run 2 | 50 | B | B | BRR | BR | BRR |
| Cont. Run 9 | Control Run 2 | 750 | B | BR | R | R | R |
| Cont. Run 10 | Control Run 2 | 3500 | B | R | R | R | R |

Note: Color changes in O$_2$ indicator
B        BBR        BR        BRR        R
blue                blue violet           red or
                    or light blue         white
⇐────────── —O$_2$ conc. %— ──────────⇒
20%                                    0%

When the oxygen indicator of the present invention was maintained for 24 hours—one month in the absence of oxygen, the indicator showed BR, BRR or R expressing the absence of oxygen under 50–3500 lux.

The oxygen indicator of Control Run 1 did not cause the color to change depending on the intensity of light. However, when the oxygen indicator of Control Run 1 was maintained for one month under anhydrous state and while being irradiated with a light, the indicator showed BBR one month later expressing the presence of oxygen. The oxygen indicator of Control Run 2 was slow in color change under limited illumination (BBR at O$_2$ concentration of 1.5% after 24 hr); in contrast, it was sensitive under ample illumination and, at the same O$_2$ concentration of 1.5%, it turned to BR under exposure to 750 lux and R under exposure to 3500 lux.

EXAMPLE 100

The oxygen indicator prepared in Example 43 was cut to a size of 15 mm×15 mm. The oxygen indicator was packed in a bag (35 mm×35 mm) formed of polyethylene film having a thickness of 30 μm and an oxygen permeability of 3500 ml/m$^2$·Atm·day. The package was sealed with an oxygen scavenger, a desiccant and air (250 ml) in a bag (250 mm×300 mm) formed of a polyvinylidene chloride-coated, oriented nylon film. The resulting sample was maintained at 25° C. The oxygen concentration and humidity in the system and the color of the oxygen indicator are shown in Table 7. The oxygen scavenger employed was the same as that of Example 63. The result are shown in Table 7.

TABLE 7

| Ex. 100 | storage time | | | | |
|---|---|---|---|---|---|
| | 0 hr. | 12 hrs. | 24 hrs. | 14 days | 1 month |
| O$_2$ conc. in the system % | 20.9 | 3.5 | 0.0 | 0.0 | 0.0 |
| relative humidity in the system % | 70 | 4 | 2 | 1 | 1 |
| color of indicator | B | B | BRR | R | R |

The color-changing rate of the oxygen indicator of Example 85 is somewhat later than that of the oxygen indicator of Example 63. However, there is no problem.

The oxygen indicator of the present invention exhibits stable function even under anhydrous conditions, and is not affected by irradiation of light.

The oxygen indicator of the present invention can be printed on paper, tapes and sheets, and can be used in the form of a tablet. Thus, it can be used in a wide variety of modes in practical applications.

The oxygen indicator of the present invention is particularly useful for maintaining articles in the absence of oxygen and its commercial value will be exhibited to the fullest under an anhydrous state and/or under irradiation of light.

Therefore, the oxygen indicator of the present invention is useful for storing metallic materials or semi-conductors which must be maintained in a dry state and for preventing rusting of metallic material. The oxygen indicator is useful for storing metallic materials while being irradiated with light, for example, for storing metallic materials in a show case.

EXAMPLE 101

Preparation of Oxygen Indicator

Each of the following three organic compounds having 3 carbon atom and containing a primary amine group and hydroxy group was used as a main component:

A: 3-amino-1,2-propanediol (APD)
B: 3-amino-2-propanol (AP2N)
C: 3-amino-1-propanol (AP1N)

Each of the amino alcohol and oleic acid given in Table 8 were added to ethyl alcohol (520 g) as a solvent. Ten Methylene Blue (2 g), Acidred (2 g) and glycerine (10 g) were added to each of the mixtures. Each of the resulting mixtures was agitated in a high speed homomixer to allow the components to be uniformly dissolved or be uniformly dispersed in the solvent, thereby obtaining an oxygen indicator composition in which the components are uniformly dispersed in the solvent.

TABLE 8

| | Oxygen Indicator Composition | | |
|---|---|---|---|
| | A | B | C |
| Main Component | APD 25 g | AP2N 25 g | AP1N 25 g |
| Acid | oleic acid 78 g | oleic acid 64 g | oleic acid 64 g |

TABLE 8-continued

| | Oxygen Indicator Composition | | |
|---|---|---|---|
| | A | B | C |
| Dyestuff | MB 2 g<br>ACD 2 g | MB 2 g<br>ACD 2 g | MB 2 g<br>ACD 2 g |
| Polyhydric<br>Alcohol | GC 10 g | GC 10 g | GC 10 g |

Each of the oxygen indicator compositions was coated on neutral paper in a coating amount of 2 g/m² by means of a Meyer bar, and dried at 100° C. for 45 seconds under hot air.

Pieces of the oxygen indicator composition-coated paper were cut to a size 20 mm×20 mm. Each of the pieces was sealed in the KON/PE bag (150 mm×200 nun) with an oxygen scavenger and air (250 ml). Each of the resulting bags was irradiated at a distance of 1 meter with a 40 W fluorescent tube at 5° C. for one month. The oxygen concentration and soybean oil (3 g) into particulate activated carbon (10 g), and packing the resulting particles and silicagel A type (15 g) by a bag (60×90 mm) formed of paper/perforated polyethylene.

TABLE 9

Oxygen Concentration and Color Change with Time

| | Storage | | | | | | |
|---|---|---|---|---|---|---|---|
| Oxygen Indicator | 1 day | 2 days | 3 days | 4 days | 5 days | 14 days | 1 month |
| O₂ Conc. in the system % | 10.4 | 3.2 | 0.2 | 0.0 | 0.0 | 0.0 | 0.0 |
| Relative Humidity in the System RH % | 6 | 3 | 1 | 1 | 1 | 1 | 1 |
| A (APD) | B | B | B | BR | BRR | R | R |
| B (AP2N) | B | B | B | BR | BRR | R | R |
| C (AP1N) | B | B | B | B | B | BR | BRR |

Color changes in O₂ indicator

| B | BBR | BR | BRR | R |
|---|---|---|---|---|
| blue | | blue violet<br>or light blue | | red or<br>white |

⇐ 20% ⇐ ⇐ —O₂ conc. %— ⇐ ⇐—0% ⇒

After the above test was completed, the bags were opened and the oxygen scavenger was withdrawn from the bags. After the atmosphere of the bags was replaced with a nitrogen gas containing 4% of oxygen, tile pieces of the oxygen indicator-coated paper were sealed in the bag with 250 ml of the nitrogen gas containing 4% of oxygen. The bag was maintained at 25° C. The oxygen concentration and the color change with time are shown in Table 10.

TABLE 10

Reversibility of Color of Oxygen Indicator

| | | Storage | | | |
|---|---|---|---|---|---|
| Oxygen indicator | Starting time | 1 day | 2 days | 3 days | 4 days |
| O₂ conc. in the system % | 0.4 | 0.6 | 0.8 | 1.1 | 1.3 |
| A (APD) | R | B | B | B | B |
| B (AP2N) | R | B | B | B | B |
| C (AP1N) | BRR | BR | BBR | B | B |

It is clear from Tables 9 and 10 that the oxygen indicator (APD and AP2N) in which a carbon atom having the primary amine is adjacent to a carbon atom having the hydroxy group is superior to the oxygen indicator (AP1N) in which a carbon atom having the primary amine is not adjacent to a carbon atom having the hydroxy group with respect to reversibility of color. That is, it is clear From Table 9 that the color change of each of APD and AP2N From B expressing tile presence of oxygen to BR, BRR or R expressing the absence of oxygen is faster than the color change of AP1N from B expressing the presence of oxygen to BR, BRR or R expressing the absence of oxygen. It is also clear from Table 10 that the color change of each of APD and AP2N from the color expressing the absence of oxygen to the color expressing the presence of oxygen is faster than the color change of AP1N from the color expressing the absence of oxygen to the color expressing the presence of oxygen.

In other words, it is clear from Tables 9 and 10 that the oxygen indicator in which a carbon atom having the primary amine is adjacent to a carbon atom having the hydroxy group is superior to the oxygen indicator in which a carbon atom having the primary amine is not adjacent to a carbon atom having the hydroxy group with respect to the response time to the presence and absence of oxygen. Therefore, the former oxygen indicator is more useful For evaluating the function of an oxygen scavenger and sealability of the bag than the latter oxygen indicator.

What is claimed is:

1. A method of indicating the presence of oxygen in an atmosphere comprising:
   contacting said atmosphere with an indicator consisting essentially of a combination of:
   (a) at least one aliphatic organic compound containing at least three carbon atoms, at least one primary amine group, and at least one hydroxyl group; and
   (b) at least one dyestuff selected from the group consisting of thiazine dyes, indigo dyes, and mixtures thereof which complexes with said organic compound in the effective presence of oxygen; and
   determining if the color of said indicator changes as an indication of the presence of oxygen.

2. An oxygen indicator consisting essentially of
   (a) at least one aliphatic organic compound having 3 or more carbon atoms and containing at least one primary amine group and at least one hydroxy group, and
   (b) at least one dyestuff selected from the group consisting of thiazine dyestuffs, indigo dyestuffs and mixtures thereof.

3. The indicator of claim 2 wherein the indicator further contains at least one organic or inorganic acid.

4. The indicator of claim 3 wherein the organic compound and the organic acid or the inorganic acid are chemically bonded to each other.

5. The indicator of claim 3 wherein the indicator is printed on a substrate.

6. The indicator of claim 3 wherein the indicator is in the form of tablet.

7. The indicator of claim 3 wherein the compound (a) is selected from the group consisting of 3-amino-1, 2-propanediol, 3-amino-1-propanol, 3-amino-2-propanol, 4-amino-3-butanol, 4-amino-1-butanol, 5-amino-4-pentanol, 5-amino-1-pentanol, 6-amino-5-hexanol, 6-amino-1-hexanol, glucosamine and 4-amino-1,2-butanediol.

8. The indicator of claim 3 wherein the compound (a) is the compound in which a carbon atom, having a primary amine, pendant therefrom, is adjacent to a carbon atom having the hydroxy group pendant therefrom.

9. The indicator of claim 3 wherein the dyestuff is selected from the group consisting of Methylene Blue, Thionine, Azure B, Azure C, Neomethylene Blue, Brilliant Arizarine Blue, Lauth's Violet, Acid Red and Indigocarmine.

10. The indicator of claim 2 wherein the indicator is printed on a substrate.

11. The indicator of claim 2 wherein the indicator is in the form of tablet.

12. The indicator of claim 2 wherein the compound (a) is selected from the group consisting of 3-amino-1,2-propanediol, 3-amino-1-propanol, 3-amino-2-propanol, 4-amino-3-butanol, 4-amino-1-butanol, 5-amino-4-pentanol, 5-amino-1-pentanol, 6-amino-5-hexanol, 6-amino-1-hexanol, glucosamine and 4-amino-1,2-butanediol.

13. The indicator of claim 2 wherein the compound (a) is the compound in which a carbon atom, having a primary amine, pendant therefrom, is adjacent to a carbon atom, having a hydroxy group pendant therefrom.

14. The indicator of claim 13 wherein the compound (a) is selected from the group consisting of 3-amino-1,2-propanediol, 3-amino-2-propanol, 4-amino-3-butanol, 5-amino-4-pentanol, 6-amino-5-hexanol, glucosamine and 3-amino-1,2-butanediol.

15. The indicator of claim 2 wherein the dyestuff is selected from the group consisting of Methylene Blue, Thionine, Azure B, Azure C, Neomethylene Blue, Brilliant Arizarine Blue, Lauth's Violet, Acid Red and Indigocarmine.

16. An oxygen indicator consisting essentially of:
   (a) at least one aliphatic organic compound containing at least three carbon atoms, at least one primary amine group, and at least one hydroxyl group; and
   (b) at least one dyestuff selected from the group consisting of thiazine dyes, indigo dyes, and mixtures thereof;
   wherein said organic compound and said dyestuff are so selected that they complex with each other in effective contact with oxygen to an extent necessary to change the color of said indicator composition as compared to the color of the indicator composition in the absence of oxygen.

17. The indicator as claimed in claim 16 wherein the proportion of said organic compound (a), relative to said dyestuff, is sufficient, in effective contact with oxygen, to complex with said dyestuff and to thereby change the color of said indicator composition as compared to the color of the indicator composition in the absence of effective contact with oxygen.

18. The indicator as claimed in claim 17 wherein said color change upon effective contact with oxygen is reversible upon the removal of oxygen from effective contact with said indicator composition.

19. The indicator as claimed in claim 16 wherein said color change upon effective contact with oxygen is reversible upon the removal of oxygen from effective contact with said indicator composition.

* * * * *